US006967253B2

United States Patent
Callens

(10) Patent No.: US 6,967,253 B2
(45) Date of Patent: Nov. 22, 2005

(54) METHOD FOR SYNTHESIS OF 5-(3-PYRIDYLMETHYLENE-)IMIDAZOLIDINE-2,4-DIONE

(75) Inventor: Roland Callens, Grimbergen (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 10/488,813

(22) PCT Filed: Sep. 2, 2002

(86) PCT No.: PCT/EP02/09886

§ 371 (c)(1),
(2), (4) Date: Mar. 5, 2004

(87) PCT Pub. No.: WO03/022834

PCT Pub. Date: Mar. 20, 2003

(65) Prior Publication Data

US 2004/0242892 A1 Dec. 2, 2004

(30) Foreign Application Priority Data

Sep. 5, 2001 (FR) .............................. 01 11637

(51) Int. Cl.⁷ .................... C07D 211/02; C07D 231/04; A61K 31/4164; A61K 31/4166
(52) U.S. Cl. .................... 546/250; 548/300.1
(58) Field of Search ........................ 546/250; 548/300.1

(56) References Cited

FOREIGN PATENT DOCUMENTS

| DE | 4 434 293 | 3/1996 | |
| EP | 1 083 170 A1 * | 8/2000 | ......... C07D/213/55 |
| EP | 1 083 170 | 3/2001 | |

OTHER PUBLICATIONS

C. Dobler et al., Tetrahedron: Asymmetry, vol. 7, No. 1, 1996, p. 117–125.
J. J. Bozell et al., Journal of Organic Chemistry, vol. 56, No. 7, 1991, p. 2584–2587.
F. Zymalkowski, Archiv. Der Pharmazie., vol. 291, No. 9, 1958, pg. 436–442.

* cited by examiner

*Primary Examiner*—Joseph K. McKane
*Assistant Examiner*—Susannah E. Lee
(74) *Attorney, Agent, or Firm*—Connolly Bove Lodge & Hutz

(57) ABSTRACT

Process for the synthesis of 5-(3-pyridylmethyl)imidazolidine-2,4-dione, according to which 5-(3-pyridylmethylene)imidazolidine-2,4-dione is subjected to a hydrogenation reaction.

18 Claims, No Drawings

100
METHOD FOR SYNTHESIS OF 5-(3-PYRIDYLMETHYLENE-)IMIDAZOLIDINE-2,4-DIONE

RELATED APPLICATIONS

This application is a Rule 371 application of PCT/EP02/09886 filed on Sep. 2, 2002 which claims benefit to French application FR 01/11637 filed Sep. 5, 2001.

The present invention relates to a process for the synthesis of 5-(3-pyridylmethyl)imidazolidine-2,4-dione. 5-(3-Pyridylmethyl)imidazolidine-2,4 dione is an intermediate which can be used for the synthesis of (3-pyridyl)alanines, in particular D-(3-pyridyl)alanine. The invention consequently also relates to a process for the synthesis of (3-pyridyl)alanine. D-(3-Pyridyl)alanine can be used as constituent of peptides, in particular in LHRH antagonists.

Patent Application EP-1 083 170-A1 stipulates that D-(3-pyridyl)alanine can be obtained by enzymatic reaction of 5-(3-pyridylmethyl)imidazolidine-2,4-dione with D-hydantoinases. However, this reference does not disclose the synthesis of 5-(3-pyridylmethyl)imidazolidine-2,4-dione.

It was consequently desirable to make available 5-(3-pyridylmethyl)imidazolidine-2,4-dione. It was particularly desirable to have available an effective and industrially exploitable process for the synthesis of 5-(3-pyridylmethyl)imidazolidine-2,4-dione. It was also desirable to have available an effective and industrially exploitable process for the synthesis of (3-pyridyl)alanines, in particular D-(3-pyridyl)alanine.

The invention consequently relates to a process for the synthesis of DL-5-(3-pyridylmethyl)imidazolidine-2,4-dione, according to which 5-(3-pyridylmethylene)imidazolidine-2,4-dione is subjected to a hydrogenation reaction.

The invention also relates to DL-5-(3-pyridylmethyl)imidazolidine-2,4-dione.

It has been founds surprisingly, that the process according to the invention makes it possible to convert 5-(3-pyridylmethylene)imidazolidine-2,4-dione to 5-(3-pyridylmethyl)imidazolidine-2,4-dione selectively and with a high yield. It is possible in particular to limit, indeed even prevent, saturation of the aromatic system of the pyridine ring. The process according to the invention can be used for the manufacture of industrial amounts of 5-(3-pyridylmethyl)imidazolidine-2,4-dione, which amounts can be used for the manufacture of (3-pyridyl)alanines, in particular of D-(3-pyridyl)alanine.

In the process according to the invention, the hydrogenation reaction is preferably carried out in the liquid phase. In this case, 5-(3-pyridylmethylene)-imidazolidine-2,4-dione is advantageously dissolved in a solvent. Solvents which can be used in the hydrogenation reaction are chosen, for example, from polar solvents. Solvents comprising at least one OH group are highly suitable. A solvent chosen from aliphatic alcohols preferably comprising from 1 to 3 carbon atoms, water, aqueous solutions of acids, preferably inorganic acids, and their mixtures has given good results. A particularly preferred solvent system comprises methanol and an aqueous hydrochloric acid solution.

The hydrogenation reaction is generally carried out in the presence of a hydrogenation catalyst. The hydrogenation catalyst is advantageously chosen from the metals from Group VIII of the Periodic Table of the Elements (IUPAC 1970). Mention will be made in particular of a catalyst comprising at least one metal chosen from palladium, platinum and rhodium. A catalyst comprising palladium is preferred. It has been found that a hydrogenation catalyst chosen from the metals from Group VIII and in particular a catalyst comprising palladium makes possible particularly selective hydrogenation of the nonaromatic double bond in 5-(3-pyridylmethylene)imidazolidine-2,4-dione.

The hydrogenation catalyst is often a supported catalyst. Supports which can be used are chosen, for example, from alumina, silica and active charcoal. A catalyst supported on active charcoal gives good results.

When the hydrogenation catalyst is a supported catalyst comprising a metal from Group VIII the metal content is generally at least 0.1% by weight with respect to the total weight of the catalyst. The metal content is often greater than or equal to 1% by weight. Preferably, the metal content is greater than or equal to 5% by weight. The metal content is generally at most 50% by weight with respect to the total weight of the catalyst.

In a very particularly preferred way, the catalyst is supported palladium, preferably supported on a support as described above, preferably exhibiting a metal content as described above.

In the hydrogenation reaction, the temperature of the reaction is generally at least −10° C. The temperature of the reaction is often at least 0° C. Preferably, this temperature is at least 20° C. The temperature of the reaction is generally at most 100° C. The temperature of the reaction is often at most 60° C. Preferably, this temperature is at most 50° C. A temperature of at most 40° C. is very particularly preferred.

In the hydrogenation reaction, the pressure of the reaction is generally at least 1 bar absolute. Preferably, the pressure is at least 1.5 bar. The pressure of the hydrogenation reaction is generally at most 10 bar absolute. Preferably, the pressure is at most 5 bar. In a particularly preferred way, it is at most 3 bar.

In the process according to the invention, use is preferably made of hydrogen as hydrogenation reactant. In this case, the pressure values of the hydrogenation reaction mentioned above generally correspond to the hydrogen pressure.

When use is made of hydrogen as hydrogenation reactant, the molar ratio of hydrogen to 5-(3-pyridylmethylene)imidazolidine-2,4-dione is generally greater than or equal to 1. This ratio is generally at most 100. Preferably, this ratio is at most 10.

In the hydrogenation reaction, the concentration of 5-(3-pyridylmethylene)imidazolidine-2,4-dione in the reaction medium is generally at least 5% by weight with respect to the total weight of the reaction medium. This concentration is often at least 10% by weight. Preferably, the concentration is at least 20% by weight. The concentration of 5-(3-pyridylmethylene)imidazolidine-2,4-dione in the reaction medium is generally at most 50% by weight with respect to the total weight of the reaction medium.

In a particularly preferred alternative form of the process according to the invention, 5-(3-pyridylmethylene)imidazolidine-2,4-dione was obtained by a condensation reaction between pyridine-3-carbaldehyde and imidazolidine-2,4-dione.

The condensation reaction between pyridine-3-carbaldehyde and imidazolidine-2,4-dione is generally carried out in the presence of a solvent, preferably an organic solvent.

If appropriate, the content of organic solvent in the reaction medium of the condensation reaction is generally at most 80% by weight with respect to the total weight of the reaction medium. Preferably, this content is at most 50% by weight.

In a first aspect, the solvent in the condensation reaction is an aqueous medium. In this aspect, use is advantageously made of a catalyst. This catalyst is generally soluble in water. A catalytic system which gives good results comprises an amino acid or an amino acid salt and an inorganic alkaline compound. Glycine is preferred as amino acid. The inorganic alkaline compound is advantageously chosen from sodium hydroxide and sodium carbonate. Sodium carbonate is preferred.

In a second aspect, the solvent in the condensation reaction comprises a polar organic solvent. The polar organic solvent generally exhibits a dipole moment of greater than 2 debyes. Solvents which can be used are in particular those capable of forming hydrogen bonds, such as polyalcohols, solvents comprising at least one amido group, or sulphones and sulphoxides. Mention may be made, by way of example, of N,N-dimethylformamide, N-methylpyrrolidone, tetramethylene sulphone, ethylene glycol, glycerol and their mixtures. Mixtures of N,N-dimethylformamide with glycerol give good results.

In a third aspect, the solvent in the condensation reaction comprises an organic solvent of low viscosity. The viscosity of the organic solvent of low viscosity is generally less than or equal to 10 mPa·s at 25° C. A viscosity of less than or equal to 5 mPa·s at 25° C. is highly suitable. A viscosity of less than or equal to 1 mPa·s at 25° C. is preferred.

In a fourth aspect, the solvent in the condensation reaction comprises an organic solvent of low polarity. The dipole moment the organic solvent of low polarity is generally at most 2 debyes. A dipole moment of less than or equal to 1.8 debyes is highly suitable. A dipole moment of less than or equal to 1 debyes is preferred.

It has been found, surprisingly, that the use of an organic solvent of low viscosity and/or of low polarity in the condensation reaction makes it possible to obtain a high yield of 5-(3-pyridylmethylene)imidazoline-2,4-dione under easy processing conditions which can be used for an industrial synthesis of 5-(3-pyridylmethylene)imidazolidine-2,4-dione.

Organic solvents which are particularly advantageous as organic solvent of low viscosity and/or polarity are chosen from linear, branched or cyclic dialkyl ethers, carboxylic esters and aromatic compounds. Mention may be made, as an example, of tetrahydrofuran, ethyl acetate, benzene, toluene and xylenes. Toluene gives good results.

The condensation reaction between pyridine-3-carbaldehyde and imidazolidine-2,4-dione is preferably carried out in the presence of a condensation catalyst. Condensation catalysts which can be used are, for example, bases, such as in particular nitrogenous bases or their salts. The catalyst is often a nitrogenous organic base, for example chosen from primary, secondary or tertiary alkylamines. Cyclic secondary amines or their salts give good results. Mention may be made, as example, of derivatives of morpholine, of pyrrolidine and of piperidine. Among these catalysts, a piperidinium salt is preferred. Piperidinium acetate is particularly well suited as condensation catalyst.

The temperature of the condensation reaction between pyridine-3-carbaldehyde and imidazolidine-2,4-dione is generally at least 50° C. Preferably, the temperature is at least 60° C. The temperature of the condensation reaction between pyridine-3-caraldehyde and imidazolidine-2,4-dione is generally at most 200° C. Preferably, the temperature is at most 150° C. A temperature of at most 130° C. is more particularly preferred.

In the process according to the invention, the condensation reaction is generally carried out at a pH of at least 7. The pH is preferably at least 8. In the process according to the invention, the condensation reaction is generally carried out at a pH of at most 12. The pH is preferably at most 10.

The invention also relates to the process for the manufacture of 5-(3-pyridylmethylene)imidazolidine-2,4-dione by the condensation reaction between pyridine-3-carbaldehyde and imidazolidine-2,4-dione as described above.

The invention also relates to a process for the synthesis of (3-pyridyl)alanine, according to which 5-(3-pyridylmethyl) imidazolidine 2,4-dione, obtained according to the process according to the invention, is subjected to a hydrolysis reaction, followed by a decarbamation reaction.

The hydrolysis reaction can be carried out, for example, by reaction with a base at a pH greater than 12.

Preferably, the hydrolysis is carried out by reaction with a hydantoinase, in particular a D-hydantoinase. In this case, the (3-pyridyl)alanine obtained is D-(3-pyridyl)alanine. The information regarding this reaction is contained in the abovementioned Patent Application EP 1 083 170-A1.

The decarbamation can be carried out, for example, by nitrosation.

(3-Pyridyl)alanine, in particular D-(3-pyridyl)alanine, obtained according to the process according to the invention can be used for the manufacture of a peptide. Conventional peptide coupling techniques can be used for the manufacture of the peptide.

The examples below are intended to illustrate the invention without, however, limiting it.

EXAMPLE 1

Synthesis of 5-(3-pyridylmethylene)imidazolidine-2,4-dione 0.1 mol of imidazolidine-2,4-dione, 3 ml of glacial acetic acid, 0.12 mol of pyridine-3-carbaldehyde and 30 ml of toluene were introduced into a round-bottomed flask. 5 ml of piperidine were also added to this mixture. The combination was heated at reflux for 17 h. After cooling, isopropanol was added. The precipitate obtained was filtered off and washed with isopropanol. The yield of 5-(3-pyridylmethylene) imidazolidine-2,4-dione was 85%.

The product obtained could be used directly, without additional purification, for use in the hydrogenation reaction.

EXAMPLE 2

Synthesis of DL-5-(3-pyridylmethyl)imidazolidine-2,4-dione 0.13 mol of 5-(3-pyridylmethylene)imidazolidine-2,4-dione obtained in accordance with the process of Example 1, 250 ml of 1N hydrochloric acid, 200 ml of methanol and 3.26 g of a catalyst composed of palladium on active charcoal (Pd concentration of 10% by weight) were introduced. The hydrogenation reaction was carried out at ambient temperature under an initial hydrogen pressure of 2.1 bar for 15 h. The reaction medium was filtered and the crude DL-5-(3-pyridylmethyl)imidazolidine-2,4-dione obtained after evaporation was crystallized from a 1:1 methanol:methyl tert-butyl ether mixture.

Yield 79%

The DL-5-(3-pyridylmethyl)imidazolidine-2,4-dione obtained could be used directly, without additional purification, for use in a hydrolysis reaction. It was suitable in particular for use in an enzymolysis reaction. The process according to the invention allows access to D-L5-(3-pyridylmethyl)imidazolidine-2,4-dione in a simple and industrially exploitable manner and with a high yield.

What is claimed is:

1. Process for the synthesis of (3-pyridyl)alanine, wherein 5-(3-pyridylmethyl)imidazolidine-2,4-dione is subjected to a hydrolysis reaction, wherein the reaction is followed by a decarbamation reaction.

2. Process according to claim 1, in which the hydrolysis is carried out by reaction with a hydantionase.

3. Process according to claim 1, in which the (3-pyridyl) alanine is D-(3-pyridyl)alanine.

4. Process according to claim 1, wherein the 5-(3-pyridylmethyl)imidazolidine-2,4-dione is obtained by the hydrogenation of 5-(3-pyridylmethylene)imidazolidine-2,4-dione.

5. Process according to claim 4, in which the hydrogenation reaction is carried out into liquid phase.

6. Process according to claim 4, in which the reaction is carried out in the presence of a hydrogenation catalyst.

7. Process according to claim 6, in which the hydrogenation catalyst is chosen from the metals from Group VIII of the Periodic Table of the Elements.

8. Process according to claim 7, in which the catalyst is supported palladium.

9. Process according to claim 4, in which the temperature of the hydrogenation reaction is from −10° C. to +100° C.

10. Process according to claim 4, in which the pressure of the hydrogenation reaction is from 1 bar to 15 bar.

11. Process according to claim 4, in which use is made of hydrogen as hydrogenation reactant.

12. Process according to claim 11, in which the molar ratio of hydrogen to 5-(3-pyridylmethylene)imidazolidine-2,4-dione is from 1 to 1000.

13. Process according to claim 4, in which the concentration of 5-(pyridylmethylene)imidazolidine-2,4-dione in the reaction medium is from 5% by weight to 50% by weight with respect to the total weight of the reaction medium.

14. Process according to claim 4, additionally comprising the manufacture of 5-(3-pyridylmethylene)imidazolidine-2,4dione by a condensation reaction between pyridine-3-carbaldehyde and imidazolidine-2,4-dione.

15. Process according to claim 14, in which the reaction between pyridine-3-carbaldehyde and imidazolidine-2,4-dione is carried out in the presence of a condensation catalyst.

16. Process according to claim 15, in which the condensation catalyst is a piperidinium salt.

17. Process according to claim 14, in which the temperature of the condensation reaction is from 50° C. to 200° C.

18. Process according to claim 14, in which the condensation reaction is carried out at a pH of 7 to 12.

\* \* \* \* \*

UNITED STATES PATENT AND TRADEMARK OFFICE
CERTIFICATE OF CORRECTION

PATENT NO. : 6,967,253 B2
DATED : November 22, 2005
INVENTOR(S) : Roland Callens It is certified that error appears in the above-identified patent and that said Letters Patent is hereby corrected as shown below:

Title page,
Item [54], Title, should read -- METHOD FOR SYNTHESIS OF 5-(3-PYRIDYLMETHYLENE)-IMIDAZOLIDINE-2,4-DIONE --.

Column 5,
Line 12, "decarbamation reaction." should read -- decarbarmation reaction --.
Line 22, "reaction is carried out into liquid phase." should read -- reaction is carried out in the liquid phase --.

Column 6,
Line 11, "of 5-(pyridylmethylene)imidazolidine-2,4-dione in" should read -- of 5-(3-pyridylmethylene)imidazolidine-2,4-dione in --.

Signed and Sealed this

Twenty-first Day of February, 2006

JON W. DUDAS
*Director of the United States Patent and Trademark Office*